United States Patent [19]

Sprinkel, Jr. et al.

[11] Patent Number: 4,717,017
[45] Date of Patent: Jan. 5, 1988

[54] PACKAGE WITH MEANS FOR RELEASING AROMATIC SUBSTANCE ON OPENING

[75] Inventors: Francis M. Sprinkel, Jr., Glen Allen; Reginald W. Newsome, Richmond, both of Va.

[73] Assignee: Philip Morris Incorporated, New York, N.Y.

[21] Appl. No.: 29,210

[22] Filed: Mar. 23, 1987

[51] Int. Cl.[4] .............. A24F 15/00; B65D 85/10; B65D 85/12

[52] U.S. Cl. .................... 206/264; 206/242; 206/606; 131/329

[58] Field of Search .......... 206/264, 242, 606, 610, 206/609; 131/359, 352, 329; 383/40

[56] References Cited

U.S. PATENT DOCUMENTS

| | | |
|---|---|---|
| 1,878,401 | 9/1932 | John . |
| 1,972,118 | 9/1934 | McDill ................ 131/329 |
| 2,046,975 | 7/1936 | Shaw et al. ................ 91/68 |
| 2,095,650 | 10/1937 | Reichenbach ................ 131/329 |
| 2,844,298 | 7/1958 | Tamarin ................ 206/264 |
| 3,303,046 | 2/1967 | Chebiniak et al. ................ 117/36.1 |
| 3,494,505 | 2/1970 | Huebner et al. ................ 222/1 |
| 3,773,248 | 11/1973 | Cecil et al. ................ 206/606 |
| 4,105,144 | 8/1978 | Lin ................ 383/40 |
| 4,145,001 | 3/1979 | Weyenberg et al. ................ 239/56 |
| 4,186,743 | 2/1980 | Steiger ................ 128/284 |
| 4,254,910 | 3/1981 | Martin ................ 239/60 |
| 4,283,011 | 8/1981 | Spector ................ 239/36 |
| 4,310,007 | 1/1982 | Auersbacher ................ 131/329 |
| 4,424,911 | 1/1984 | Resnick ................ 215/365 |
| 4,463,770 | 8/1984 | Thompson ................ 131/329 |
| 4,484,768 | 11/1984 | Norfleet ................ 283/1 B |
| 4,487,801 | 12/1984 | Turnbull et al. ................ 428/313.5 |
| 4,493,869 | 1/1985 | Sweeny et al. ................ 428/201 |
| 4,528,226 | 7/1985 | Sweeny ................ 428/40 |
| 4,606,956 | 8/1986 | Charbonneau et al. ................ 428/40 |

*Primary Examiner*—Joseph Man-Fu Moy
*Attorney, Agent, or Firm*—Jeffrey H. Ingerman

[57] ABSTRACT

A package, such as a cigarette pack, is provided with a receptacle for containing a fragrance or flavor to be released upon initial opening by the consumer. The receptacle is provided by attaching to the polymeric film circumscribing the sealed package, in the area overlying the tear tape, an additional layer of polymeric film. The fragrance or flavor is entrapped between the polymeric film and the extra polymeric layer and is released when the tear tape is pulled through the receptacle to unseal the pack. The receptacle can be provided with compartments to minimize leakage or to allow the flavor or fragrance to be kept in two or more relatively inert components which react on contact to form the fragrance or flavor or, possibly, to form a propellant to disperse the fragrance or flavor.

21 Claims, 8 Drawing Figures

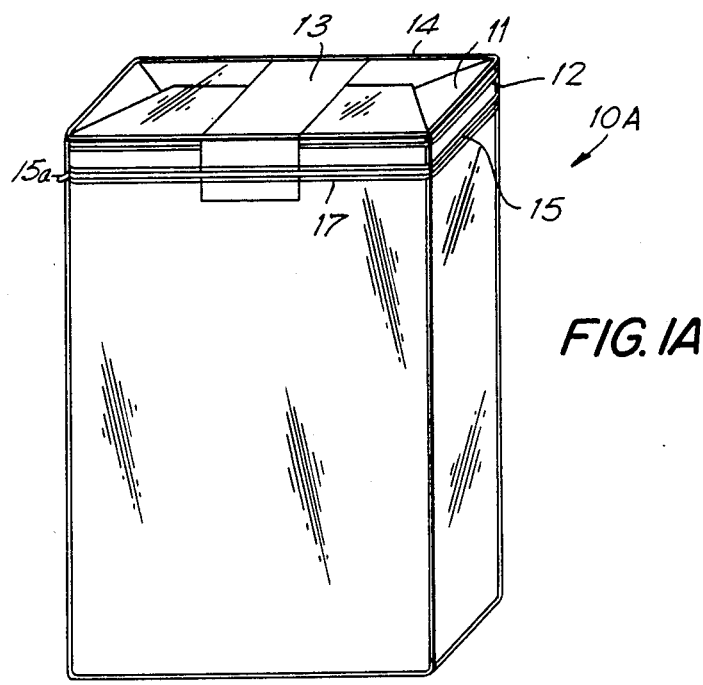
FIG. IA
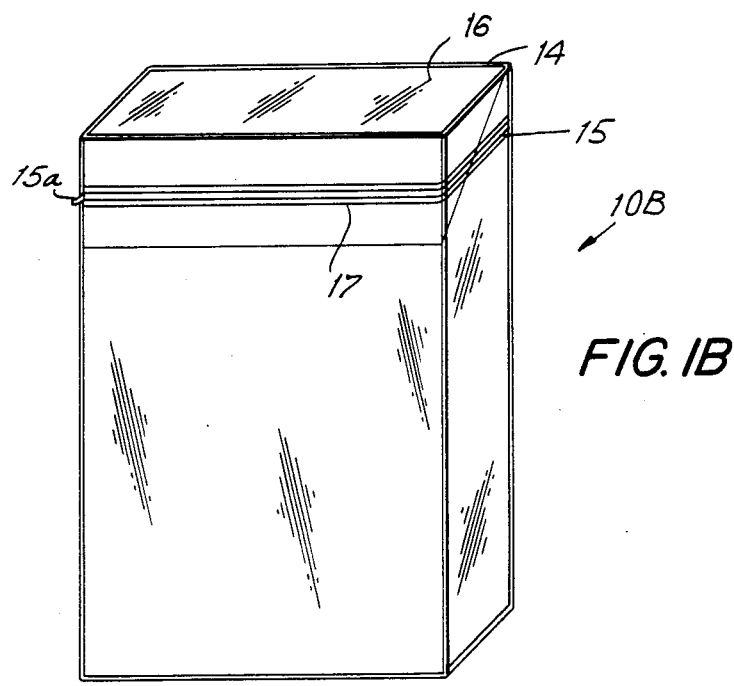
FIG. IB

PACKAGE WITH MEANS FOR RELEASING AROMATIC SUBSTANCE ON OPENING

BACKGROUND OF THE INVENTION

This invention relates to packages. More particularly, the present invention relates to a cigarette pack having means for releasing aromatic substances, such as flavorants or fragrances, when the pack is unsealed for the first time.

Cigarettes are generally sold in two types of packs. One type of pack is the so-called "soft pack" in which a group of twenty or twenty-five cigarettes is wrapped in foil and the foil is in turn wrapped by a paper wrapper on which brand and other information is printed. The second type of pack is a relatively stiff paperboard box having a hinged lid and sometimes referred to as a FLIP-TOP® box. Both types of packs are typically overwrapped by a clear polymeric film such as polyethylene to maintain cigarette freshness. A "tear tape", i.e., a strip generally of a polymeric material such as polypropylene, and usually colored to stand out, is provided for opening the polymeric wrapping. The tear tape usually projects from the wrapping and is pulled by the smoker to slit open the polymeric wrapping. Other materials such as paper and foils can be used for the tear tape, and foils can also be used as the overwrap.

If the wrapping of a cigarette pack is slit open just after the pack has been made, a strong aroma of fresh tobacco is emitted. As more time passes from manufacture to opening of the pack, the aroma of freshness on opening decreases even though the cigarettes are still fresh. Therefore, a smoker may feel that one particular cigarette pack is fresher than another, even though both are fresh.

Further, it is well known that flavorant materials—e.g., menthol—can be added to cigarettes. However, some flavorants are highly volatile and excess amounts of those flavorants must be added if the amount remaining when the cigarette is smoked is to be sufficient to produce the desired flavor effect. It would be desirable to be able to add less excess flavorant to such cigarettes.

It would be desirable to be able to provide a cigarette pack or other package that releases an aroma of freshness upon opening.

It would also be desirable to be able to add volatile flavorants to cigarettes in relatively small amounts that are sealed against evaporation until the cigarette pack is opened.

SUMMARY OF THE INVENTION

It is an object of this invention to provide a cigarette pack or other package that releases an aroma of freshness upon opening.

It is also an object of this invention to provide for the addition of volatile flavorants to cigarettes in relatively small amounts that are sealed against evaporation until the cigarette pack is opened.

In accordance with the invention, there is provided a package for releasing a volatile material upon being opened. The package comprises a container and a sealing film circumscribing the container for preserving the freshness of contents of the container prior to the opening of the package. Film slitting means, such as a tear tape, is interposed between the container and the sealing film and protrudes from the sealing film to allow a consumer to slit the sealing film and open the package. Receptacle means overlies the film slitting means and contains a volatile material such that the film slitting means ruptures the receptacle means while slitting the sealing film, releasing the volatile substance.

In a preferred embodiment, the package is a cigarette pack.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIG. 1A is a front, top perspective view of a cigarette soft pack in accordance with this invention;

FIG. 1B is a front, top perspective view of a cigarette box pack in accordance with this invention;

DETAILED DESCRIPTION OF THE INVENTION

Figure 2:
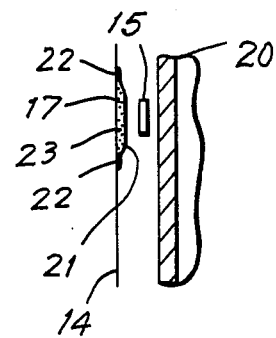
FIG. 2 is a fragmentary vertical cross-sectional view of one embodiment of a cigarette pack according to this invention.

A conventional cigarette soft pack 10A and a conventional hinged-lid cigarette box 10B, both modified according to the present invention, are shown in FIGS. 1A and 1B, respectively. As shown in FIG. 1A, soft pack 10A includes a foil wrapper 11 which is wrapped around the cigarettes (not visible) in the pack. A paper wrapper 12, which is usually printed with brand and other information, is wrapped around foil layer 11. A seal 13 is adhered across the top of the pack to both foil layer 11 and paper wrapper 12. A layer of generally transparent film 14, of a polymeric material such as polyethylene, circumscribes the entire pack 10A to maintain cigarette freshness.

Similarly, hinged-lid pack 10B, shown in FIG. 1B, includes a hinged-lid box 16, usually of relatively stiff paperboard, circumscribed by film 14 to maintain freshness.

In both packs 10A, 10B, a tear tape 15, of a polymeric material such as polypropylene, is applied to the inner side of the film 14 before film 14 is wrapped around pack 10A, 10B. Tape 15 is usually denser and stronger than film 14 and is applied so that its end 15A protrudes from the pack (at the point of overlap of the ends of film 14) so that a smoker can grasp end 15A and pull it to slit open film 14.

In accordance with this invention, receptacle 17 overlies tape 15. Receptacle 17 can be outside film 14, or between film 14 and tape 15, and is filled with an aromatic substance, or components thereof, as described in more detail below. When tape 15 is pulled to slit film 14, receptacle 17 is also slit open, releasing the sustance contained therein for dispersal into the air or onto the cigarettes in the pack.

Aromatic substances are thus physically held in a container that is leak free, even though a substance may include volatile liquids as well as gases. This provides an advantage over chemical encapsulation or microencapsulation methods. In fact, receptacle 17 can be used to protect microencapsulated substances from leakage until the pack is opened.

The substance can be a fragrance which conveys a certain desired impression, such as freshness, to the smoker on opening of the pack. The fragrance may or may not be one of tobacco in order to convey the desired impression. Alternatively, the substance can be a flavorant which permeates the cigarettes in the pack when it is released. This would be particularly useful in the case of volatile flavorants which might dissipate if applied to the cigarettes before packaging. A single aromatic substance may provide both olfactory and taste sensations as it is released both outward and inward into the pack.

Receptacle 17 may be divided into compartments, as described in more detail below, in which case the aromatic substance may be provided as separate components that react when the compartments are ruptured to produce the desired substance. The reaction may also produce a propellant to aid in dispersing the substance. A substance would be provided in components if it were so volatile that it might escape even from a sealed compartment but its components were less volatile, if its characteristics were such that leakage of the components would be less undesirable than leakage of the substance, or if it were desired to release a propellant.

A substance might also be provided in compartments, even in its final form, to minimize the possibility of leakage. If there are several compartments, it is unlikely they would all develop leaks.

A first embodiment of the invention is shown in FIG. 2, which shows cigarette container 20 (either the foil 11 and paper 12 of soft pack 10A or the box 16 of pack 10B), film 14, and tear tape 15 between them for slitting film 14. Receptacle 17 is formed by a layer 21, preferably of polymeric material which may or may not be the same as that of film 14, and preferably clear. Layer 21 is adhered to film 14 at points 22, preferably by heat sealing, but could also be adhered by a suitable adhesive that would not react with volatile substance 23. At least one of layer 21 and film 14 is coated with an acetate ester to improve heat sealing.

Figure 3:
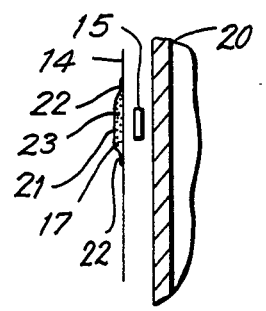
FIG. 3 is a fragmentary vertical cross-sectional view of a second embodiment of a cigarette pack according to this invention.

A second embodiment of the invention, shown in FIG. 3, is similar to the embodiment of FIG. 2, except that layer 21 is fastened to the outer side of film 14.

Figure 4:
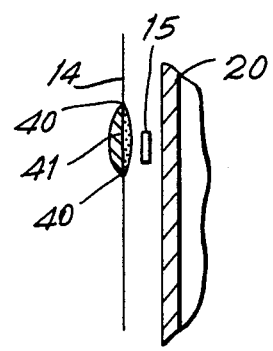
FIG. 4 is a fragmentary vertical cross-sectional view of a third embodiment of a cigarette pack according to this invention.
Figure 5:
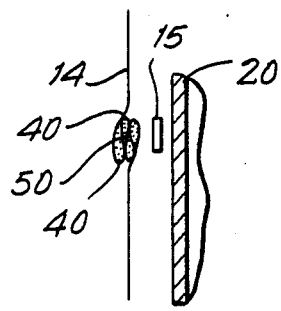
FIG. 5 is a fragmentary vertical cross-sectional view of a fourth embodiment of a cigarette pack according to this invention.

A third embodiment of the invention, shown in FIG. 4, does not use an additional layer such as layer 21. Instead, film 14 is doubled back on itself and adhered at points 40, by heat-sealing or suitable adhesive, to form two-compartment receptacle 41. By doubling film 14 back on itself more than once, multiple compartment receptacles of any even number of compartments can be created. As shown in FIG. 5, in a fourth embodiment, doubling film 14 back a second time creates four-compartment receptacle 50.

Figure 6:
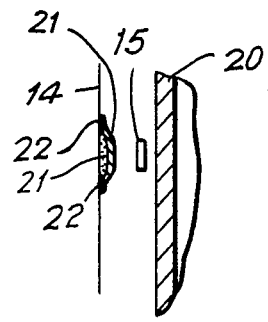
FIG. 6 is a fragmentary vertical cross-sectional view of a fifth embodiment of a cigarette pack according to this invention.
Figure 7:
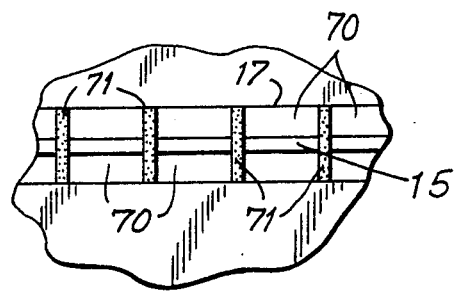
FIG. 7 is a fragmentary elevational view of a sixth embodiment of a cigarette pack according to this invention.

In a fifth embodiment of the invention, shown in FIG. 6, multiple compartments are created by adhering multiple layers 21 of the type shown in FIG. 2. This embodiment can also be constructed with the receptacle on the outer side of film 14 as in FIG. 3, or with some compartments inside film 14 and others outside film 14 (not shown).

In a sixth embodiment, which can be used in conjunction with any of the above-described embodiments, compartments 70 are created by heat-sealing vertical lines 71 at horizontally spaced-apart locations along the receptacle 17. Sealed vertical lines 71 can also, of course, be provided using a suitable adhesive.

In the embodiments of FIGS. 4 and 5, receptacle 17 is necessarily formed of the same material as film 14. However, in the embodiments of FIGS. 2, 3, 6 and 7, it may be formed of other materials, including, but not limited to, metallic foils. The material used for receptacle 17 may be chosen based on the characteristics of the substance 23 to be contained. In particular, if substance 23 would react adversely to or with the polyethylene in film 14, layers 21 would be made of some other material that would not react. In such a case, layers 21 would have to be arranged in such a way that substance 23 is separated from film 14.

Depending on which of the embodiments above is used, receptacle 17 may be assembled during the packaging operation or it may be preassembled and fed to the packaging machinery as needed. Some embodiments may require one or the other of those alternatives, while others may allow either alternative.

Although described above in the context of a cigarette pack, the present invention has application in other types of packaging. A package according to the invention can be used to contain any items in connection with which it would be appropriate to release an aromatic substance on opening the package.

Thus, a package is provided which can be used to release an aromatic substance on first opening by the consumer. One skilled in the art will appreciate that the present invention can be practiced by other than the described embodiments, which are presented for purposes of illustration and not of limitation, and the present invention is limited only by the claims which follow.

What is claimed is:

1. A cigarette pack for releasing a volatile material upon being opened, said cigarette pack comprising:
   a cigarette container;
   a sealing film circumscribing said cigarette container for preserving, prior to said cigarette pack being opened, the freshness of cigarettes contained in said cigarette container;
   film slitting means interposed between said cigarette container and said sealing film and protruding from said sealing film for allowing a smoker to slit said sealing film to open said cigarette pack; and
   receptacle means overlying said film slitting means for containing volatile material, such that said film slitting means ruptures said receptacle means while slitting said sealing film, releasing said volatile material.

2. The cigarette pack of claim 1 wherein said receptacle means is formed by laminating a receptacle layer to said sealing film overlying said film slitting means.

3. The cigarette pack of claim 2 wherein said receptacle layer is laminated to an inner side of said sealing film between said film slitting means and said sealing film.

4. The cigarette pack of claim 2 wherein said receptacle layer is laminated to an outer side of said sealing film.

5. The cigarette pack of claim 2 wherein said receptacle layer is of the same material as said sealing film.

6. The cigarette pack of claim 2 wherein said receptacle layer is of a metallic foil material.

7. The cigarette pack of claim 1 wherein said receptacle means is formed by folding over and adhering a portion of said sealing film overlying said film slitting means.

8. The cigarette pack of claim 7 wherein said folded-over portion of said sealing film is adhered by heat sealing.

9. The cigarette pack of claim 1 wherein said volatile substance is a flavorant, said flavorant being dispersed throughout said cigarette pack when said receptacle means is ruptured.

10. The cigarette pack of claim 1 wherein said volatile substance is a fragrance for producing an olfactory sensation in the smoker.

11. The cigarette pack of claim 10 wherein said olfactory sensation is one of freshness.

12. The cigarette pack of claim 11 wherein said olfactory sensation is one of tobacco.

13. The cigarette pack of claim 1 wherein said receptacle means comprises a plurality of compartments.

14. The cigarette pack of claim 13 wherein said volatile material is broken down into components, each of said components being contained in at least one of said compartments separated from other of said components, said components reacting with one another to form said volatile material when said compartments are ruptured.

15. The cigarette pack of claim 14 wherein said components react to form a propellant substance for dispersing said volatile material.

16. The cigarette pack of claim 7 wherein said folded-over portion is folded upon itself at least once, each fold producing two compartments.

17. The cigarette pack of claim 16 wherein said volatile material is broken down into components, each of said components being contained in at least one of said compartments separated from other of said components, said components reacting with one another to form said volatile material when said compartments are ruptured.

18. The cigarette pack of claim 17 wherein said components react to form a propellant substance for dispersing said volatile material.

19. The cigarette pack of claim 1 wherein said cigarette container is a soft pack.

20. The cigarette pack of claim 1 wherein said cigarette container is a box having a hinged lid.

21. A package for releasing a volatile material upon being opened, said package comprising:
  a container;
  a sealing film circumscribing said container for preserving, prior to said package being opened, the freshness of contents of said container;
  film slitting means interposed between said container and said sealing film and protruding from said sealing film for allowing a consumer to slit said sealing film to open said package; and
  receptacle means overlying said film slitting means for containing volatile material, such that said film slitting means ruptures said receptacle means while slitting said sealing film, releasing said volatile material.

* * * * *